(12) United States Patent
Li et al.

(10) Patent No.: US 10,807,940 B2
(45) Date of Patent: Oct. 20, 2020

(54) METHOD FOR PREPARING P-HYDROXYCINNAMATE BY USING IONIC LIQUID FOR CATALYTIC LIGNIN DEPOLYMERIZATION

(71) Applicant: South China University of Technology, Guangzhou (CN)

(72) Inventors: Xuehui Li, Guangzhou (CN); Zhangmin Li, Guangzhou (CN); Zhenping Cai, Guangzhou (CN); Jinxing Long, Guangzhou (CN); Weijie Zhao, Guangzhou (CN); Hongwei Ma, Guangzhou (CN)

(73) Assignee: South China University of Technology (CN)

( * ) Notice: Subject to any disclaimer, the term of this patent is extended or adjusted under 35 U.S.C. 154(b) by 0 days.

(21) Appl. No.: 16/642,959

(22) PCT Filed: Nov. 21, 2017

(86) PCT No.: PCT/CN2017/112102
§ 371 (c)(1),
(2) Date: Feb. 28, 2020

(87) PCT Pub. No.: WO2019/041583
PCT Pub. Date: Mar. 7, 2019

(65) Prior Publication Data
US 2020/0181058 A1    Jun. 11, 2020

(30) Foreign Application Priority Data

Aug. 31, 2017    (CN) .......................... 2017 1 0769753

(51) Int. Cl.
*C07C 67/30* (2006.01)
*B01J 31/02* (2006.01)
*C07C 69/732* (2006.01)

(52) U.S. Cl.
CPC .......... *C07C 67/30* (2013.01); *B01J 31/0281* (2013.01); *C07C 69/732* (2013.01)

(58) Field of Classification Search
CPC ..... C07C 67/30; C07C 69/732; B01J 31/0281
See application file for complete search history.

(56) References Cited

U.S. PATENT DOCUMENTS

2019/0203012 A1* 7/2019 Shi .......................... C08H 6/00

OTHER PUBLICATIONS

Prado, R., et al., Lignin oxidatoin and depolymrisaiton in ionic liquids, 2016, Green Chemistry, vol. 18, pp. 834-841 (Year: 2016).*

(Continued)

*Primary Examiner* — Yate' K Cutliff
(74) *Attorney, Agent, or Firm* — The Webb Law Firm (57) ABSTRACT

The present invention discloses a method for preparing p-hydroxycinnamate by using an ionic liquid for catalytic lignin depolymerization comprising: 1) preparation of a halogen metal-based ionic liquid: preparing the halogen metal-based ionic liquid by reacting an alkylimidazole chloride with a metal chloride by heating the same to 30° C. to 80° C. with stirring; and 2) catalytic depolymerization of lignin: mixing the halogen metal-based ionic liquid and lignin with an alcohol, and after $N_2$ replacement, heating the solution to 140° C. to 200° C. and reacting the solution for 4-8 h while stirring to prepare high value-added chemicals with p-hydroxycinnamate as a main product. The present invention has advantages of a simple process, mild conditions, environmental kindness, and high selectivity for a main product. The ionic liquid is simple in preparation, has a good atom economy, and is recyclable. Under optimal conditions, the yield of p-hydroxycinnamate can reach 40-80 mg/g.

10 Claims, 2 Drawing Sheets

(56) References Cited

OTHER PUBLICATIONS

Li et al., "Application of Ionic Liquids in Lignin Processing", Chemistry and Industry of Forest Products, 2015, pp. 163-170, vol. 35, No. 2. (English Language Abstract).

Yan et al., "Understanding lignin treatment in dialkylimidazolium-based ionic liquid-water mixtures" Chinese Masters's Theses Full-text Database (Engineering Science and Technology I), 2015, pp. 509-517, vol. 196. (English Language Translation).

* cited by examiner

METHOD FOR PREPARING P-HYDROXYCINNAMATE BY USING IONIC LIQUID FOR CATALYTIC LIGNIN DEPOLYMERIZATION

CROSS-REFERENCE TO RELATED APPLICATIONS

This application is the United States national phase of International Application No. PCT/CN/2017/112102 filed Nov. 21, 2017, and claims priority to Chinese Patent Application No. 201710769753.2 filed Aug. 31, 2017, the disclosures of each of which are hereby incorporated by reference in their entirety.

BACKGROUND OF THE INVENTION

The present invention relates to the field of efficient utilization of agricultural wastes and high-value utilization of renewable resources, in particular to a method for preparing p-hydroxycinnamate by using an ionic liquid for selective catalytic lignin depolymerization.

FIELD OF THE INVENTION

With the development of society and the improvement of people's living standards, the demand for disposable fossil resources has gradually increased, and the environment has been challenged. Renewable energy has become the focus of attention. Biomass energy, as the only renewable carbon energy that can be converted into energy and chemicals, has attracted more and more interest. In the past few decades, research on biomass mainly focused on the biorefinement of cellulose and hemicellulose, in which generation of the fuel ethanol has been industrialized.

Lignin, as the second most abundant biomass resources after cellulose, is an important renewable aromatic compound material. It has been widely studied in recent years. At present, the main methods for studying lignin valorization include pyrolysis, oxidation, hydrogenation, hydrolysis, etc. However, most of these methods aim at obtaining mixed phenolic products or bio-oils, which results in problems such as complex product components, difficult subsequent processing, large energy consumption, and low quality. Herbaceous agricultural and forestry wastes have a large output and a low utilization rate in China. Currently, most of them are burned as a source of energy. Therefore, it is of great application value to selectively depolymerize agricultural and forestry lignin to obtain high value-added chemicals, which is being recognized by more and more people.

The structural formula of p-hydroxycinnamate is as follows:

where n=0, 1, 2, 3, 4, 5, 6, 7. Hydroxycinnamate is an organic synthesis intermediate and a pharmaceutical intermediate, and can be used to synthesize the anti-adrenalin drug esmolol. As a fine chemical, it is widely used in food, chemical and other industries. Because it contains an olefin structure, it has a good application prospect in polymer materials and other fields. Recently, OKAHATA Co., Ltd. of Japan has extended the application of p-hydroxycinnamate to the field of electronics and optical fiber communications, making p-hydroxycinnamate an excellent touch screen and high-end fiber optic material, by virtue of the characteristics of very good transparency, high photosensitivity, and excellent thermal stability of p-hydroxycinnamate. However, the current synthesis of p-hydroxycinnamate is mainly realized through a series of organic reactions. This process is not only tedious and often involves the use of corrosive protonic acids or precious metal catalysts, but is not high in the yield as well.

SUMMARY OF THE INVENTION

For avoiding the disadvantages of the prior art, the present invention aims to provide a method for preparing p-hydroxycinnamate by using an ionic liquid for catalytic lignin depolymerization, so as to solve the problems of poor selectivity and low efficiency in the catalytic depolymerization of lignin. This has achieved the efficient utilization of agricultural and forestry wastes and the highly selective catalytic depolymerization of lignin, so that the reaction conversion has reached 40% to 50%.

This method adopts herbaceous lignin widely present in agricultural and forestry wastes as a raw material, and uses a metal-base ionic liquid synthesized from metal chloride and imidazole chloride as a catalyst, with the ionic liquid having low cost and economical synthesis process. Besides, this method uses C1-C4 fatty alcohol as a solvent, which not only makes the product p-hydroxycinnamate have higher selectivity, but also can realize product separation and catalyst recycling.

The object of the present invention is achieved through the following technical solution:

A method for preparing p-hydroxycinnamate by using an ionic liquid for catalytic lignin depolymerization is provided, comprising the following steps:

1) preparation of an ionic liquid: preparing a halogen metal-based ionic liquid by mixing an alkylimidazole chloride with a metal halide at a molar ratio of 1:1 to 2:1 at 30° C. to 80° C. and then extracting and drying; and 2) depolymerization of lignin: mixing the halogen metal-based ionic liquid obtained in step 1) and an organosolv lignin, adding a solvent thereto, and after $N_2$ replacement, heating the solution to 140° C. to 200° C. and reacting the solution for 4-8 h while stirring, filtering and extracting the reaction solution to obtain a biochemical, and concentrating and separating the biochemical to obtain p-hydroxycinnamate. extracting the reaction solution to obtain a biochemical, and concentrating and separating the biochemical to obtain p-hydroxycinnamate.

To further achieve the object of the present invention, preferably, the metal halide in step 1) is aluminum chloride, ferric chloride, chromium chloride, manganese chloride, cobalt chloride, nickel chloride, copper chloride or zinc chloride.

Preferably, the cation of the halogen metal-based ionic liquid is an alkylimidazole, and the anion is $[FeCl_4]^-$, $[CrCl_4]^-$, $[AlCl_4]^-$, $[MnCl_4]^{2-}$, $[CoCl_4]^{2-}$, $[NiCl_4]^{2-}$, $[CuCl_4]^{2-}$ or $[ZnCl_4]^{2-}$.

Preferably, the structural formula of the halogen metal-based ionic liquid is as follows:

n = 0-6; M = Fe, Cr, Al n = 0-6; M = Mn, Co, Ni, Cu, Zn

Preferably, the mixing time at 30° C. to 80° C. is 3-8 h, and the extractant in step 1) is ethyl acetate.

Preferably, the solvent is a C1-C7 fatty alcohol, the stirring speed is 150-600 r/min, and the lignin is an agricultural and forestry herbaceous lignin.

Preferably, the agricultural and forestry herbaceous lignin is bagasse, wheat straw, corn stalk, corn cob, rice straw, bamboo or Chinese miscanthus; during the preparation, the organosolv lignin is extracted by the following method: in mass parts, adding 100 parts of deionized water, 150-250 parts of ethanol, 0.5-1.5 parts of sulfuric acid, and 15-30 parts of agricultural and forestry waste powder to a reactor, reacting at 150° C. to 200° C. for 2-6 h, then filtering and separating, adding deionized water to the liquid phase, and then filtering and separating to obtain a solid that is the organosolv lignin.

Preferably, the step of filtering and extracting the reaction solution to obtain a biochemical is as follows: adding deionized water to the reaction solution to precipitate unreacted lignin, filtering, and then drying the filter residue at 60° C. to 80° C.; evaporating the filtrate to dryness, adding water before transferring to a separatory funnel, extracting with ethyl acetate three times, and evaporating the extracted phase to dryness to obtain the biochemicals of p-hydroxycinnamate, ferulate, acid compounds, aldehyde compounds and ester derivatives.

Preferably, the alkylimidazole chloride is prepared according to the following steps: mixing N-methylimidazole and 1-chloroalkane at a molar ratio of (0.1-1):(0.12-1.2), stirring at room temperature for 12-24 h, then raising the temperature to 60° C. to 100° C., and continuing to stir for 24-36 h to obtain a mixed solution; washing the mixed solution with ether, and then drying in vacuum to obtain the alkylimidazole chloride.

Preferably, the halogen metal-based ionic liquid [$C_n$mim][$MCl_4$] is prepared as follows: mixing 2-50 mmol of ferric chloride or aluminum chloride or chromium chloride with an equivalent amount of the alkylimidazole chloride, stirring at 30° C. to 50° C. for 3-6 h, then extracting with 5-15 mL of dichloromethane, evaporating the solvent off the resulting solution, and drying in vacuum at 60° C. to 80° C. for 12-24 h to obtain the halogen metal-based ionic liquid [$C_n$mim][$MCl_4$].

The halogen metal-based ionic liquid [$C_n$mim]$_2$[$MCl_4$] is prepared as follows: mixing 2-50 mmol of manganese chloride or cobalt chloride or nickel chloride or copper chloride or zinc chloride with alkylimidazole chloride at a molar ratio of 1.2, stirring at 60° C. to 80° C. for 3-6 h, then extracting with 5-15 mL of dichloromethane, evaporating the solvent off the resulting solution, and drying in vacuum at 60° C. to 80° C. for 12-24 h to obtain the halogen metal-based ionic liquid [$C_n$mim]$_2$[$MCl_4$].

The structural formula of p-hydroxycinnamate in step (2) is as follows:

p-hydroxycinnamate, where n=0, 1, 2, 3.

The principle of the present invention is as follows: based on the fact that the H units (p-hydroxyphenyl lignin) in herbaceous lignin are mostly connected to lignin by ester bonds, while other G units (guaiacyl lignin) and S units (syringyl lignin) are linked by more carbon-carbon and ether bonds, the present invention utilizes the finding that the halogen metal-based ionic liquid has good selective fracturing performance for the ester bonds in lignin, thereby achieving the purpose of selectively fracturing depolymerized lignin. The present invention solves the problems of poor selectivity, low efficiency, difficult separation of target products, and difficult recovery of catalysts in the catalytic depolymerization of lignin, and realizes the efficient utilization of agricultural and forestry wastes and the highly selective catalytic depolymerization of lignin.

Compared with the prior art, the present invention has the following advantages and effects:

The halogen metal-based ionic liquid catalytic system provided by the present invention realizes selective catalytic depolymerization of bagasse and other agricultural and forestry waste lignin to obtain p-hydroxycinnamate, achieving the reaction conversion of 40% to 50%, the yield of volatile products of 100-150 mg/g, the yield of methyl p-hydroxycinnamate of 60-80 mg/g, and the corresponding selectivity of 55% to 75%. The main product p-hydroxycinnamate has high commercial application value, and can be used as a pharmaceutical intermediate and a fine chemical; methyl p-hydroxycinnamate can also be used in liquid crystal and optical fiber materials. The halogen metal-based ionic liquid has the advantages of simple preparation, good atom economy, low cost, and reusability. The regenerated lignin (residue) after the reaction is not significantly changed in structure, and can be further depolymerized to obtain other chemicals or bio-oils.

DESCRIPTION OF THE INVENTION

In order to better understand the present invention, it will be further described below in conjunction with drawings and examples; however, the embodiments of the present invention are not limited thereto.

Example 1

A method for preparing p-hydroxycinnamate by using an ionic liquid for catalytic lignin depolymerization was used, comprising the following steps:

(1) preparation of a halogen metal-based ionic liquid [C$_4$mim][FeCl$_4$]: mixing 20 mmol of ferric chloride with an equivalent amount of 1-butyl-4-methylimidazole chloride C$_4$mimCl, stirring at 30° C. for 3 h, then extracting with 5 mL of dichloromethane, evaporating the solvent off the resulting solution, and drying in vacuum at 60° C. for 12-24 h to obtain the halogen metal-based ionic liquid [C$_4$mim][FeCl$_4$];

(2) extraction of organosolv lignin: adding 250 mL of ethanol, 100 mL of deionized water, 1.0 g of sulfuric acid, and 20 g of bagasse powder to a 500 mL stainless steel reactor, reacting at 160° C. for 4 h, then filtering and separating, adding deionized water to the liquid phase, and then filtering and separating to obtain a solid that was the organosolv lignin; and (3) catalytic depolymerization of lignin: mixing 2 mmol of the halogen metal-based ionic liquid [C$_n$mim][FeCl$_4$] obtained in step (1) and 0.5 g of the organosolv lignin from bagasse extracted in step (2), adding 10 mL of methanol as a solvent thereto, and after N$_2$ replacement for three times, heating the solution to 180° C., and reacting the solution for 6 h while stirring at 500 r/min; after the reaction, cooling the reactor to room temperature, pouring out the mixture of the reactor, then adding 40 mL of deionized water to the mixture, filtering, washing the filter residue with methanol several times, and then drying and weighing to calculate the lignin conversion; evaporating the liquid phase to dryness, adding water to the chemicals left before transferring them to a separatory funnel, extracting with ethyl acetate (30 mL×3) to obtain biochemicals, adding an internal standard thereto, and taking a small sample for GC-MS analysis of products and yield; concentrating the remaining chemicals under reduced pressure, and separating by a chromatography column ($v_{ethyl\ acetate}$:$v_{petroleum\ ether}$=2:1) to obtain methyl p-hydroxycinnamate.

Figure 1:
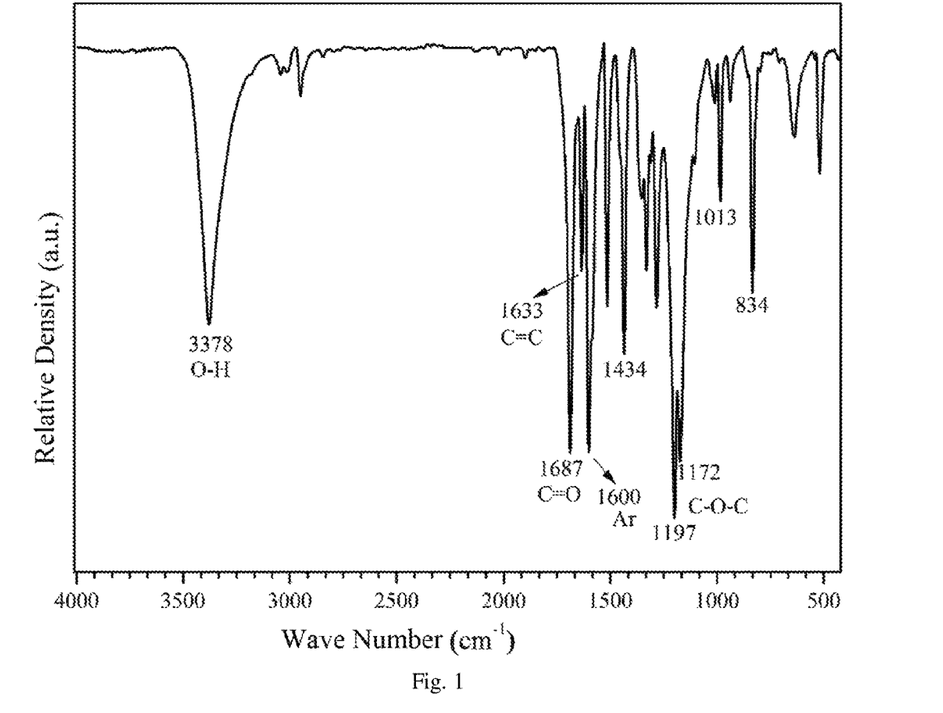
FIG. 1 is an infrared spectrogram of the main product obtained by separation in Example 1.
Figure 2:
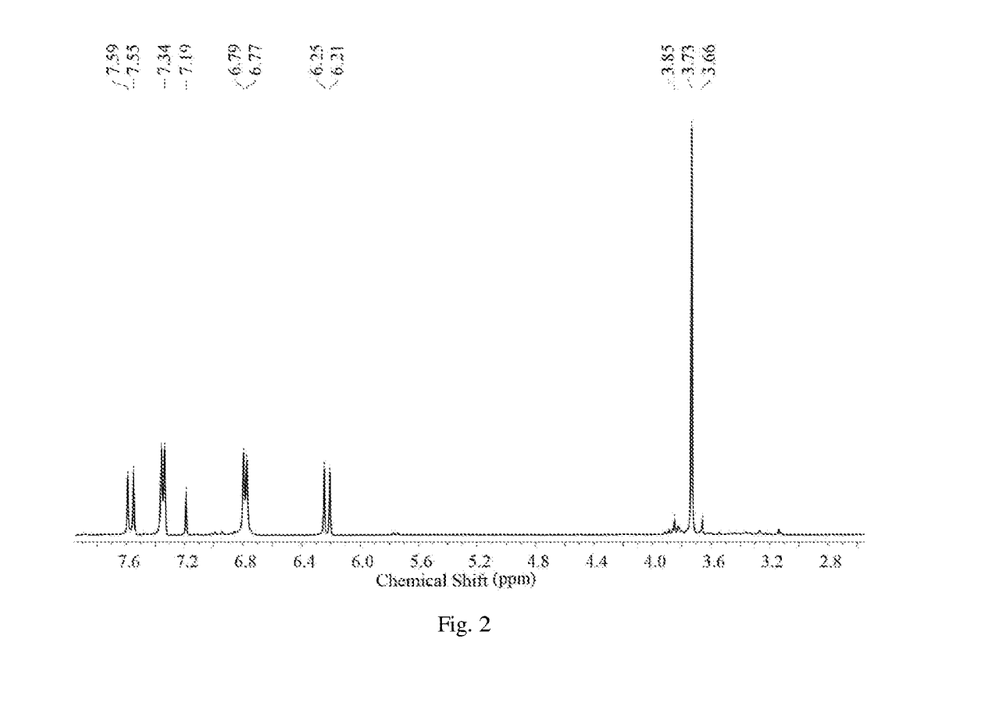
FIG. 2 is a $^1$H NMR diagram of the main product obtained by separation in Example 1.
Figure 3:
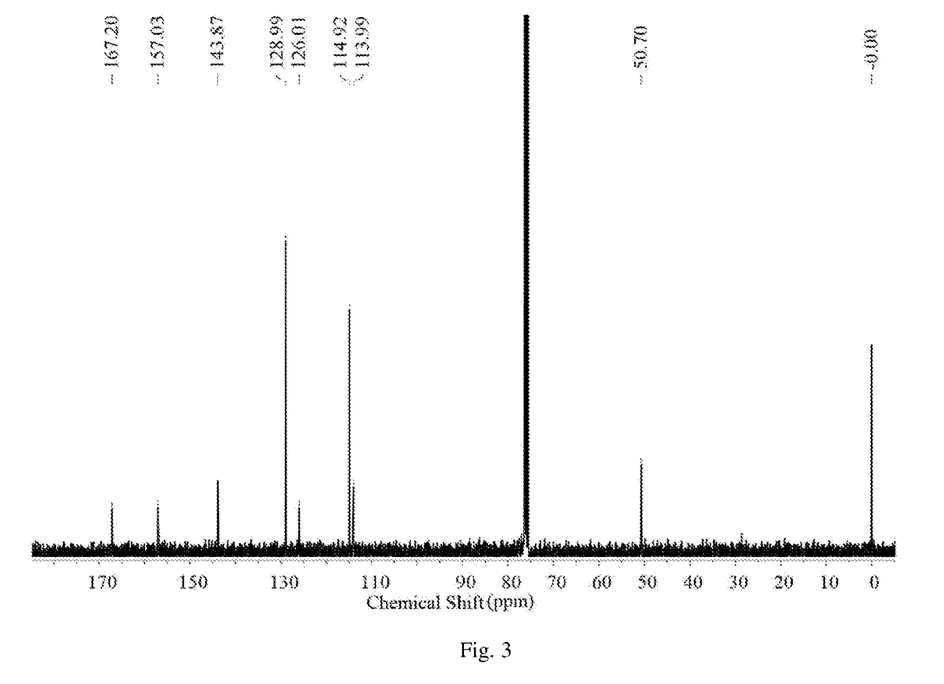
FIG. 3 is a $^{13}$C NMR diagram of the main product obtained by separation in Example 1.
Figure 4:
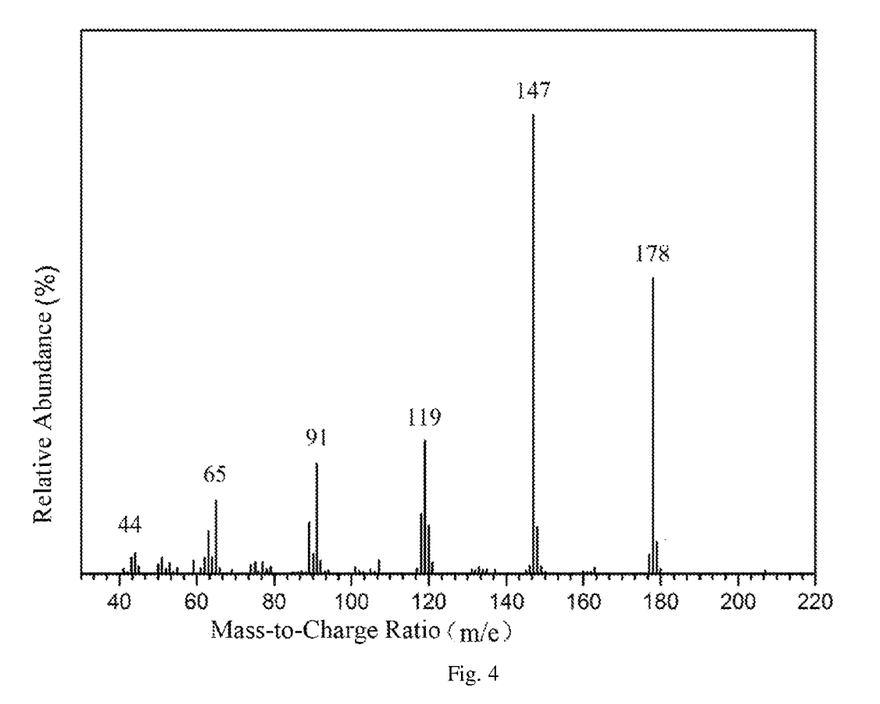
FIG. 4 is a mass spectrogram of the main product obtained by separation in Example 1.

Characterized by infrared, nuclear magnetic resonance, and mass spectrometries, as shown in FIGS. 1-4, the obtained product was confirmed to be methyl p-hydroxycinnamate. It was showed by calculation that the conversion of lignin was 48%, the yield of volatile products was 120 mg/g, the yield of methyl p-hydroxycinnamate was 87 mg/g, and the corresponding selectivity was 73%. Other products obtained by GC-MS were methyl ferulate, vanillin, syringaldehyde, and other acids and esters.

Example 2

Example 2 was different from Example 1 in the following aspects:

(1) preparation of a halogen metal-based ionic liquid [C$_n$mim][AlCl$_4$]: mixing 10 mmol of aluminum chloride with an equivalent amount of 1-ethyl-4-methylimidazole chloride C$_2$mimCl, stirring at 80° C. for 12 h, then extracting with 15 mL of dichloromethane, evaporating the solvent off the resulting solution, and drying in vacuum at 70° C. for 12-24 h to obtain the halogen metal-based ionic liquid [C$_2$mim][AlCl$_4$];

(2) extraction of organosolv lignin: adding 200 mL of ethanol, 100 mL of deionized water, 1.5 g of sulfuric acid, and 30 g of corn stover powder to a 1 L stainless steel reactor, reacting at 120° C. for 6 h, then filtering and separating, adding deionized water to the liquid phase, and then filtering and separating to obtain a solid that was the organosolv lignin; and (3) catalytic depolymerization of lignin: mixing 5 mmol of the halogen metal-based ionic liquid [C$_2$mim][AlCl$_4$] obtained in step (1) and 1 g of the organosolv lignin extracted in step (2), adding 25 mL of methanol as a solvent thereto, and after N$_2$ replacement for three times, heating the solution to 200° C., and reacting the solution for 4 h while stirring at 500 r/min; after the reaction, cooling the reactor to room temperature, pouring out the contents of the reactor, then adding 150 mL of deionized water to the contents, filtering, washing the filter residue with ethanol several times, and then drying and weighing to calculate the lignin conversion; evaporating the liquid phase to dryness, adding water to the chemicals left before transferring them to a separatory funnel, extracting with ethyl acetate (100 mL×3) to obtain biochemicals, adding an internal standard thereto, and taking a small sample for GC-MS analysis of products and yield; concentrating the remaining chemicals under reduced pressure, and separating by a chromatography column ($v_{ethyl\ acetate}$:$v_{petroleum\ ether}$=2:1) to obtain ethyl p-hydroxycinnamate.

It was shown by calculation that the lignin conversion was 43%, the yield of volatile products was 104 mg/g, the yield of ethyl p-hydroxycinnamate was 69 mg/g, and the corresponding selectivity was 66%. Other products obtained by GC-MS were ethyl ferulate, vanillin, syringaldehyde, and other acids and esters. A series of characterization was carried out on the products obtained by the separation, with the results similar to those of Example 1.

Example 3

Example 3 was different from Example 1 in the following aspects:

(1) preparation of a halogen metal-based ionic liquid [C$_6$mim][CoCl$_4$]: mixing 20 mmol of cobalt chloride with an equivalent amount of 1-hexalkyl-4-methylimidazole chloride [C$_6$mim]Cl, stirring at 80° C. for 8 h, then extracting with 15 mL of dichloromethane, evaporating the solvent off the resulting solution, and drying in vacuum at 80° C. for 12-24 h to obtain the halogen metal-based ionic liquid [C$_6$mim][CoCl$_4$];

(2) extraction of organosolv lignin: adding 1000 mL of ethanol, 500 mL of deionized water, 8.0 g of sulfuric acid, and 200 g of wheat straw powder to a 2 L stainless steel reactor, reacting at 150° C. for 6 h, then filtering and separating, adding deionized water to the liquid phase, and then filtering and separating to obtain a solid that was the organosolv lignin; and (3) catalytic depolymerization of lignin: mixing 10 mmol of the halogen metal-based ionic liquid [C$_6$mim][CoCl$_4$] obtained in step (1) and 2.5 g of the organosolv lignin extracted in step (2), adding 30 mL of n-propanol as a solvent thereto, and after N$_2$ replacement for three times, heating the solution to 160° C., and reacting the solution for 8 h while stirring at 500 r/min; after the reaction, cooling the reactor to room temperature, pouring out the contents of the reactor, then adding 300 mL of deionized water to the contents, filtering, washing the filter residue with methanol several times, and then drying and weighing to calculate the lignin conversion; evaporating the liquid phase to dryness, adding water to the chemicals left before transferring them to a separatory funnel, extracting with ethyl acetate (30 mL×3) to obtain biochemicals, adding an internal standard thereto, and taking a small sample for GC-MS analysis of products and yield; concentrating the remaining chemicals under reduced pressure, and separating by a chromatography column ($v_{ethyl\ acetate}$:$v_{petroleum\ ether}$=2:1) to obtain propyl p-hydroxycinnamate.

It was shown by calculation that the lignin conversion was 41%, the yield of volatile products was 96 mg/g, the yield of propyl p-hydroxycinnamate was 61 mg/g, and the corresponding selectivity was 63%. Other products obtained by GC-MS were propyl ferulate, vanillin, syringaldehyde, and other acids and esters. A series of characterization was carried out on the products obtained by the separation, with the results similar to those of Example 1.

Example 4

Example 4 was different from Example 1 in the following aspects:

(1) preparation of a halogen metal-based ionic liquid $[C_1mim]_2[CuCl_4]$: the halogen metal-based ionic liquid $[C_1mim]_2[CuCl_4]$ was prepared as follows: mixing 25 mmol of copper chloride with 50 mmol of 1-methyl-4-methylimidazole chloride $[C_1mim]Cl$, stirring at 60° C. for 6 h, then extracting with 10 mL of dichloromethane, evaporating the solvent off the resulting solution, and drying in vacuum at 60° C. for 12-24 h to obtain the halogen metal-based ionic liquid $[C_1mim]_2[CuCl_4]$;

(2) extraction of organosolv lignin: adding 200 mL of ethanol, 100 mL of deionized water, 1.0 g of sulfuric acid, and 25 g of straw powder to a 500 mL stainless steel reactor, reacting at 200° C. for 4 h, then filtering and separating, adding deionized water to the liquid phase, and then filtering and separating to obtain a solid that was the organosolv lignin; and (3) catalytic depolymerization of lignin: mixing 20 mmol of the halogen metal-based ionic liquid $[C_1mim]_2[CuCl_4]$ obtained in step (1) and 5 g of the organosolv lignin extracted in step (2), adding 50 mL of n-butanol as a solvent thereto, and after $N_2$ replacement for three times, heating the solution to 180° C., and reacting the solution for 6 h while stirring at 500 r/min; after the reaction, cooling the reactor to room temperature, pouring out the contents of the reactor, then adding 200 mL of deionized water to the contents, filtering, washing the filter residue with n-butanol several times, and then drying and weighing to calculate the lignin conversion; evaporating the liquid phase to dryness, adding water to the chemicals left before transferring them to a separatory funnel, extracting with ethyl acetate (30 mL×3) to obtain biochemicals, adding an internal standard thereto, and taking a small sample for GC-MS analysis of products and yield; concentrating the remaining chemicals under reduced pressure, and separating by a chromatography column ($v_{ethyl\ acetate}:v_{petroleum\ ether}=2:1$) to obtain butyl p-hydroxycinnamate.

It was shown by calculation that the lignin conversion was 38%, the yield of volatile products was 76 mg/g, the yield of ethyl p-hydroxycinnamate was 48 mg/g, and the corresponding selectivity was 63%. Other products obtained by GC-MS were butyl ferulate, vanillin, syringaldehyde, and other acids and esters. A series of characterization was carried out on the products obtained by the separation, with the results similar to those of Example 1.

Example 5

(1) Preparation of a halogen metal-based ionic liquid $[C_3mim][FeCl_4]$: mixing 20 mmol of ferric chloride with 20 mmol of 1-propyl-3-methylimidazole chloride $[C_3mim]Cl$, stirring at 40° C. for 8 h, then extracting with 5 mL of dichloromethane, evaporating the solvent off the resulting solution, and drying in vacuum at 60° C. for 12-24 h to obtain the halogen metal-based ionic liquid $[C_3mim][FeCl_4]$;

(2) extraction of organosolv lignin: adding 220 mL of ethanol, 100 mL of deionized water, 1.2 g of sulfuric acid, and 25 g of bamboo powder to a 500 mL stainless steel reactor, reacting at 120° C. for 6 h, then filtering and separating, adding deionized water to the liquid phase, and then filtering and separating to obtain a solid that was the organosolv lignin; and (3) catalytic depolymerization of lignin: mixing 2 mmol of the halogen metal-based ionic liquid $[C_3mim][FeCl_4]$ obtained in step (1) and 5 g of the organosolv lignin extracted in step (2), adding 50 mL of ethanol as a solvent thereto, and after $N_2$ replacement for three times, heating the solution to 180° C., and reacting the solution for 6 h while stirring at 500 r/min; after the reaction, cooling the reactor to room temperature, pouring out the contents of the reactor, then adding 200 mL of deionized water to the contents, filtering, washing the filter residue with ethanol several times, and then drying and weighing to calculate the lignin conversion; evaporating the liquid phase to dryness, adding water to the chemicals left before transferring them to a separatory funnel, extracting with ethyl acetate (30 mL×3) to obtain biochemicals, adding an internal standard thereto, and taking a small sample for GC-MS analysis of products and yield; concentrating the remaining chemicals under reduced pressure, and separating by a chromatography column ($v_{ethyl\ acetate}:v_{petroleum\ ether}=2:1$) to obtain ethyl p-hydroxycinnamate.

It was shown by calculation that the lignin conversion was 42%, the GC yield was 8.3%, the yield of ethyl p-hydroxycinnamate was 42 mg/g, and the corresponding selectivity was 51%. Other products obtained by GC were ethyl ferulate, vanillin, syringaldehyde, and other acids and esters. A series of characterization was carried out on the products obtained by the separation, with the results similar to those of Example 1.

Example 6

Reusability of the ionic liquid catalyst $[C_4mim][FeCl_4]$ in Example 1: mixing 4 mmol of the halogen metal-based ionic liquid $[C_4mim][FeCl_4]$ and 1 g of the bagasse organosolv lignin, adding 10 mL of methanol as a solvent thereto, and after $N_2$ replacement for three times, heating the solution to 180° C., and reacting the solution for 6 h while stirring; after the reaction, cooling the reactor to room temperature, pouring out the contents of the reactor, then adding 200 mL of deionized water to the contents, filtering, washing the filter residue with water several times, and then drying and weighing to calculate the lignin conversion; transferring the filtrate to a separatory funnel, extracting with ethyl acetate (30 mL×3), adding an internal standard to the ethyl acetate phase, and making GC-MS analysis of products and yield; concentrating the lower aqueous phase by rotary evaporation, extracting with dichloromethane, then evaporating dichloromethane before drying in vacuum, and using the dried catalyst to repeat the above experimental process for four times. The results are shown in Table 1 below.

TABLE 1

| Number of repetitions | 1 | 2 | 3 | 4 | 5 |
|---|---|---|---|---|---|
| Lignin conversion (%) | 48 | 46 | 45 | 43 | 44 |
| Yield of volatile products (mg/g) | 120 | 114 | 106 | 101 | 105 |
| Yield of p-hydroxycinnamate (mg/g) | 78 | 75 | 69 | 66 | 63 |
| Selectivity of p-hydroxycinnamate (%) | 65 | 66 | 65 | 65 | 62 |

Example 7

Investigation of the reuse of regenerated lignin (residue) after reaction: adding 0.5 g of the regenerated lignin obtained after the reaction in Example 1, 1.5 mmol of 1-butylsulfonyl-3-methylimidazole hydrogen sulfate ([BSmim][HSO$_4$]), and 50 mL of ethanol (v$_{ethanol}$:v$_{water}$=4:1) to a 100 ml high-pressure reactor, and after N$_2$ replacement for three times, heating the solution to 250° C., and reacting the solution for 30 min while mechanical stirring; after the reaction, cooling the reactor to room temperature, pouring out the contents of the reactor, then adding 300 mL of deionized water to the contents, filtering, washing the filter residue with ethanol several times, and then drying and weighing to calculate the lignin conversion; evaporating the liquid phase to dryness, adding water to the chemicals left before transferring them to a separatory funnel, extracting with ethyl acetate (30 mL×3) to obtain biochemicals, adding an internal standard thereto, and taking a small sample for GC-MS analysis of products and yield. It was shown by calculation that the lignin conversion was 72%, the yield of volatile products was 123 mg/g, and the yield of aromatic compounds was 89 mg/g. The other products obtained by GC-MS were mainly ethyl ferulate, vanillin, syringaldehyde, and other acids and esters from the G and S structural units.

It can be seen from the above examples that the present invention achieved the object of selectively obtaining high value-added chemicals (p-hydroxycinnamate) directly from renewable bagasse and other herbaceous lignin based on the finding that the halogen metal-based ionic liquid could selectively tailoring of the H unit linked with lignin by an ester bond without breaking other C—O or C—C bonds. The results showed that the conversion of the herbaceous lignin was 40% to 50%, and the yield of volatile products was 80-110 m/g, wherein the yield of the main product hydroxycinnamate was 40-80 mg/g and the selectivity was 50% to 70%. The process has the obvious advantages such as simple catalyst preparation, atom economy, and easy recovery and reuse of the catalyst.

In addition, the regenerated lignin (residue) after the reaction was not significantly changed in structure, and could be used for further catalytic depolymerization to obtain other chemicals or bio-oils; Hence, lignin could be depolymerized step by step to achieve efficient utilization of agricultural and forestry wastes. Compared with the prior art, this method has the advantages such as mild conditions, high product selectivity, little damage to the structure of lignin, and easy separation of products. The principle is that this method provides a new path for the high-value utilization of lignin The embodiments of the present invention are not limited to the above examples, and any other alterations, modifications, substitutions, combinations, and simplifications made without departing from the spirit and principle of the present invention should all be equivalent replacements and included in the scope of protection of the present invention.

The invention claimed is:

1. A method for preparing p-hydroxycinnamate by using an ionic liquid for catalytic lignin depolymerization, wherein the method comprises:
preparation of an ionic liquid: preparing a halogen metal-based ionic liquid by mixing an alkylimidazole chloride with a metal halide at a molar ratio of 1:1 to 2:1 at 30° C. to 80° C. and then extracting and drying; and
depolymerization of lignin: mixing the halogen metal-based ionic liquid and an organosolv lignin, adding a solvent thereto, and after N$_2$ replacement, heating the solution to 140° C. to 200° C. and reacting the solution for 4-8 h while stirring, filtering and extracting the reaction solution to obtain a biochemical, and concentrating and separating the biochemical to obtain p-hydroxycinnamate.

2. The method for preparing p-hydroxycinnamate by using an ionic liquid for catalytic lignin depolymerization according to claim 1, wherein the metal halide is aluminum chloride, ferric chloride, chromium chloride, manganese chloride, cobalt chloride, nickel chloride, copper chloride or zinc chloride.

3. The method for preparing p-hydroxycinnamate by using an ionic liquid for catalytic lignin depolymerization according to claim 1, wherein the cation of the halogen metal-based ionic liquid is an alkylimidazole, and the anion is [FeCl$_4$]$^-$, [CrCl$_4$]$^-$, [AlCl$_4$]$^-$, [MnCl$_4$]$^{2-}$, [CoCl$_4$]$^{2-}$, [NiCl$_4$]$^{2-}$, [CuCl$_4$]$^{2-}$ or [ZnCl$_4$]$^{2-}$.

4. The method for preparing p-hydroxycinnamate by using an ionic liquid for catalytic lignin depolymerization according to claim 1, wherein the structural formula of the halogen metal-based ionic liquid is as follows:

5. The method for preparing p-hydroxycinnamate by using an ionic liquid for catalytic lignin depolymerization according to claim 1, wherein the mixing time at 30° C. to 80° C. is 3-8 h, and an extractant used in the preparation of an ionic liquid is ethyl acetate.

6. The method for preparing p-hydroxycinnamate by using an ionic liquid for catalytic depolymerization according to claim 1, wherein the solvent is a C1-C7 fatty alcohol, the stirring speed is 150-600 r/min, and the lignin is an agricultural and forestry herbaceous lignin.

7. The method for preparing p-hydroxycinnamate by using an ionic liquid for catalytic lignin depolymerization according to claim 6, wherein the agricultural and forestry herbaceous lignin is bagasse, wheat straw, corn stalk, corn cob, rice straw, bamboo or Chinese *miscanthus*; during the preparation, the organosolv lignin is extracted by the following method: in mass parts, adding 100 parts of deionized water, 150-250 parts of ethanol, 0.5-1.5 parts of sulfuric acid, and 15-30 parts of agricultural and forestry waste powder to a reactor, reacting at 150° C. to 200° C. for 2-6 h, then filtering and separating, adding deionized water to the liquid phase, and then filtering and separating to obtain a solid that is the organosolv lignin.

8. The method for preparing p-hydroxycinnamate by using an ionic liquid according for catalytic lignin depolymerization according to claim 1, wherein the step of filtering and extracting the reaction solution to obtain a biochemical comprises: adding deionized water to the reaction solution to precipitate unreacted lignin, filtering, and then drying the filter residue at 60° C. to 80° C.; evaporating the filtrate to dryness, adding water before transferring to a separatory funnel, extracting with ethyl acetate three times, and evaporating the extracted phase to dryness to obtain the biochemicals of p-hydroxycinnamate, ferulate, acid compounds, aldehyde compounds and ester derivatives.

9. The method for preparing p-hydroxycinnamate by using an ionic liquid for catalytic lignin depolymerization according to claim 1, wherein the alkylimidazole chloride is prepared by: mixing N-methylimidazole and 1-chloroalkane at a molar ratio of (0.1-1):(0.12-1.2), stirring at room temperature for 12-24 h, then raising the temperature to 60° C. to 100° C., and continuing to stir for 24-36 h to obtain a mixed solution; washing the mixed solution with ether, and then drying in vacuum to obtain the alkylimidazole chloride.

10. The method for preparing p-hydroxycinnamate by using an ionic liquid for catalytic lignin depolymerization according to claim 4, wherein a halogen metal-based ionic liquid $[C_n\text{mim}][MCl_4]$ is prepared by: mixing 2-50 mmol of ferric chloride or aluminum chloride or chromium chloride with an equivalent amount of the alkylimidazole chloride, stirring at 30° C. to 50° C. for 3-6 h, then extracting with 5-15 mL of dichloromethane, evaporating the solvent off the resulting solution, and drying in vacuum at 60° C. to 80° C. for 12-24 h to obtain the halogen metal-based ionic liquid $[C_n\text{mim}][MCl_4]$; and a halogen metal-based ionic liquid $[C_n\text{mim}]_2[MCl_4]$ is prepared as follows: mixing 2-50 mmol of manganese chloride or cobalt chloride or nickel chloride or copper chloride or zinc chloride with alkylimidazole chloride at a molar ratio of 1.2, stirring at 60° C. to 80° C. for 3-6 h, then extracting with 5-15 mL of dichloromethane, evaporating the solvent off the resulting solution, and drying in vacuum at 60° C. to 80° C. for 12-24 h to obtain the halogen metal-based ionic liquid $[C_n\text{mim}]_2[MCl_4]$.

* * * * *

UNITED STATES PATENT AND TRADEMARK OFFICE
CERTIFICATE OF CORRECTION

PATENT NO. : 10,807,940 B2
APPLICATION NO. : 16/642959
DATED : October 20, 2020
INVENTOR(S) : Xuehui Li et al.

It is certified that error appears in the above-identified patent and that said Letters Patent is hereby corrected as shown below:

On the Title Page

Column 2, item (56), Other Publications, Line 1, Delete "oxidatoin" and insert -- oxidation --

Column 2, item (56), Other Publications, Line 1, Delete "depolymrisaiton" and insert -- depolymerisation --

In the Specification

Column 1, Line 10, Delete "PCT/CN/2017/112102" and insert -- PCT/CN2017/112102 --

In the Claims

Column 10, Line 41, Claim 6, Delete "catalytic depolymerization" and insert -- catalytic lignin depolymerization --

Column 10, Line 60, Claim 8, After "liquid" delete "according"

Column 12, Line 11, Claim 10, Delete "1.2," and insert -- 1:2, --

Column 12, Line 16, Claim 10, Delete "mim]$_2$ [MCl$_4$]." and insert -- mim]$_2$[MCl$_4$]. --

Signed and Sealed this
Fourth Day of May, 2021

Drew Hirshfeld
*Performing the Functions and Duties of the
Under Secretary of Commerce for Intellectual Property and
Director of the United States Patent and Trademark Office*